(12) United States Patent
Abe et al.

(10) Patent No.: US 7,261,975 B2
(45) Date of Patent: Aug. 28, 2007

(54) NON-AQUEOUS ELECTROLYTIC SOLUTION AND LITHIUM SECONDARY BATTERY USING THE SAME

(75) Inventors: Koji Abe, Yamaguchi (JP); Takaaki Kuwata, Yamaguchi (JP)

(73) Assignee: Ube Industries, Ltd., Yamaguchi (JP)

( * ) Notice: Subject to any disclaimer, the term of this patent is extended or adjusted under 35 U.S.C. 154(b) by 26 days.

(21) Appl. No.: 10/572,571

(22) PCT Filed: Sep. 17, 2004

(86) PCT No.: PCT/JP2004/013687

§ 371 (c)(1), (2), (4) Date: Mar. 17, 2006

(87) PCT Pub. No.: WO2005/029631

PCT Pub. Date: Mar. 31, 2005

(65) Prior Publication Data

US 2007/0054185 A1    Mar. 8, 2007

(30) Foreign Application Priority Data

Sep. 17, 2003    (JP) ............................. 2003-324100

(51) Int. Cl.
H01M 10/08    (2006.01)
(52) U.S. Cl. ...................... 429/199; 429/188; 429/324; 429/326; 429/330; 252/62.2
(58) Field of Classification Search ................ 429/199; 252/62.2
See application file for complete search history.

(56) References Cited

U.S. PATENT DOCUMENTS

| | | | | |
|---|---|---|---|---|
| 6,503,662 B1 * | 1/2003 | Hamamoto et al. | ......... | 429/326 |
| 6,537,697 B2 * | 3/2003 | Kida et al. | ................. | 429/199 |
| 6,866,966 B2 * | 3/2005 | Hamamoto et al. | ......... | 429/340 |
| 6,881,522 B2 * | 4/2005 | Hamamoto et al. | ......... | 429/332 |
| 2007/0054185 A1 * | 3/2007 | Abe et al. | ................... | 429/200 |

FOREIGN PATENT DOCUMENTS

| | | |
|---|---|---|
| JP | 09-050822 | 2/1997 |
| JP | 11-329490 | 11/1999 |
| JP | 11-329496 | 11/1999 |
| JP | 2000-003724 | 1/2000 |
| JP | 2000-156243 | 6/2000 |
| JP | 2000-323169 | 11/2000 |
| WO | WO 03/077351 | 9/2003 |

OTHER PUBLICATIONS

International Search Report, PCT/JP2004/013687, Jan. 25, 2005.
International Preliminary Report on Patentability and Written Opinion of the International Searching Authority, PCT/JP2004/0113687, Jul. 6, 2006.

* cited by examiner

Primary Examiner—Mark Ruthkosky
(74) Attorney, Agent, or Firm—Nixon Peabody LLP; Jeffrey L. Costellia

(57) ABSTRACT

The present invention provides a lithium secondary battery which is improved particularly in cycle characteristics. Disclosed is a lithium secondary battery which uses a non-aqueous electrolytic solution obtained by dissolving electrolyte salt in a non-aqueous solvent. The non-aqueous electrolytic solution further contains a pentafluorophenyloxy compound represented by the formula (I), and vinylene carbonate and/or 1,3-propanesultone.

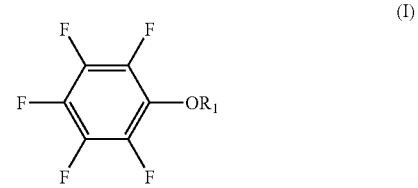

(I)

In the formula (I), $R_1$ is a substituent selected from the group consisting of an alkylcarbonyl group having 2 to 12 carbon atoms, an alkoxycarbonyl group having 2 to 12 carbon atoms, an aryloxycarbonyl group having 7 to 18 carbon atoms, and an alkanesulfonyl group having 1 to 12 carbon atoms. At least one hydrogen atom of the substituent can be substituted with a halogen atom or an aryl group having 6 to 18 carbon atoms.

10 Claims, No Drawings

NON-AQUEOUS ELECTROLYTIC SOLUTION AND LITHIUM SECONDARY BATTERY USING THE SAME

FIELD OF THE INVENTION

The present invention relates to a non-aqueous electrolytic solution advantageously used in preparation of a lithium secondary battery excellent in battery performance such as cycle characteristics, electric capacity, and storage characteristics. The invention also relates to a lithium secondary battery using the same.

BACKGROUND OF THE INVENTION

The lithium secondary battery has recently been widely used for example, as an electric source for driving small-sized electronics. The lithium secondary battery has a basic structure comprising a positive electrode, a negative electrode and a non-aqueous electrolytic solution. The positive electrode preferably comprises a complex oxide of lithium such as $LiCoO_2$, and the negative electrode preferably comprises a carbon material or metallic lithium. A carbonate such as ethylene carbonate (EC) or propylene carbonate (PC) has been advantageously used in the non-aqueous electrolytic solution for the lithium secondary battery.

The recent secondary battery requires a further improvement on battery performance such as cycle characteristics of the battery and electric capacity.

In a lithium secondary battery, $LiCoO_2$, $LiMn_2O_4$ or $LiNiO_2$ is used as a positive electrode material. A process of charging the battery causes a local oxidation and decomposition reaction of a part of a solvent contained in a non-aqueous electrolytic solution. The decomposition product inhibits an ordinary electrochemical reaction of the battery to lower battery performance. The reason is considered that a solvent is electrochemically oxidized along the interface between the positive electrode material and the non-aqueous electrolytic solution.

In a lithium secondary battery, a highly crystallized carbon material such as natural or artificial graphite is used as a negative electrode material. A process of charging the battery causes a reduction and decomposition reaction of a part of solvents contained in a non-aqueous electrolytic solution on a surface of the negative electrode. Ethylene carbonate (EC) is widely used as the non-aqueous electrolytic solvent. Ethylene carbonate may partially be reduced and decomposed to lower battery performance while repeating charge and discharge.

U.S. Patent Application Publication No. 2002/0110735 discloses an invention of adding a pentafluorobenzene compound having an electron-donating group such as 2,3,4,5,6-pentafluoroanisole to a non-aqueous electrolytic solution to improve battery performance of the lithium secondary battery. The obtained capacity retention of a coin-shaped cell after 200 cycles is 80%, which is not necessarily satisfactory.

Japanese Patent Provisional Publication No. 7-302614 discloses a chemical method for protecting a battery from excessive charge. The publication describes that a non-aqueous electrolytic solution can contain 2,3,4,5,6-pentafluoroanisole as a redox agent according to the method. However, the publication is silent with respect to cycle characteristics.

Japanese Patent Provisional Publication No. 11-329490 describes that a non-aqueous electrolytic solution can contain a specific pentafluorobenzene derivative to improve battery performance of the lithium secondary battery, such as cycle characteristics, electric capacity, and storage characteristics.

U.S. Pat. No. 5,626,981 discloses that a non-aqueous electrolytic solution can contain vinylene carbonate to improve storage stability of the lithium secondary battery.

U.S. Pat. No. 6,033,809 discloses that a non-aqueous electrolytic solution can contain 1,3-propanesultone and/or 1,4-butanesultone to improve battery performance such as cycle characteristics, electric capacity, and storage characteristics as well as performance at low temperature.

DISCLOSURE OF THE INVENTION

Problems to be Solved by the Invention

An object of the present invention is to provide a lithium secondary battery improved in cycle characteristics for a long term, and a non-aqueous electrolytic solution advantageously used in preparation of a lithium secondary battery improved in the cycle characteristics.

The present inventors have completed an invention about a lithium secondary battery improved in cycle characteristics. The battery can be prepared by adding a pentafluorophenyloxy compound (i.e., the compound represented by the formula (I)) such as pentafluorophenyl methanesulfonate to a non-aqueous electrolytic solution. The inventors have filed a patent application (PCT/JP03/02991) for the invention.

The present inventors have studied to provide a lithium secondary battery further improved in cycle characteristics, and reached the present invention.

Means to Solve the Problem

The present invention provides a non-aqueous electrolytic solution comprising an electrolyte salt in a non-aqueous solvent, wherein the non-aqueous electrolytic solution further contains a pentafluorophenyloxy compound represented by the formula (I), and vinylene carbonate (VC) and/or 1,3-propanesultone (PS):

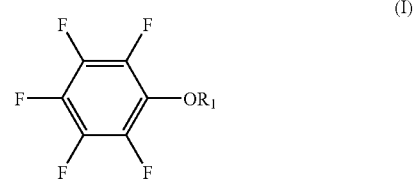

in which $R_1$ is a substituent selected from the group consisting of an alkylcarbonyl group having 2 to 12 carbon atoms, an alkoxycarbonyl group having 2 to 12 carbon atoms, an aryloxycarbonyl group having 7 to 18 carbon atoms, and an alkanesulfonyl group having 1 to 12 carbon atoms (particularly 1 to 6 carbon atoms), and at least one hydrogen atom of the substituent can be substituted with a halogen atom or an aryl group having 6 to 18 carbon atoms.

The invention also provides a lithium secondary battery comprising a positive electrode, a negative electrode and a non-aqueous electrolytic solution comprising an electrolyte salt in a non-aqueous solvent, wherein the non-aqueous electrolytic solution further contains a pentafluorophenyloxy compound represented by the formula (I), and vinylene carbonate and/or 1,3-propanesultone.

EFFECT OF THE INVENTION

The present invention can provide a lithium secondary battery improved in battery performance, particularly cycle characteristics.

BEST MODE FOR CARRYING OUT THE INVENTION

In the present invention, a non-aqueous electrolytic solution contains a pentafluorophenyloxy compound in addition to vinylene carbonate and/or 1,3-propanesultone. The non-aqueous electrolytic solution contains the pentafluorophenyloxy compound in an amount of preferably not less than 0.01 wt. %, more preferably not less than 0.1 wt. %, and most preferably not less than 0.3 wt. %. The non-aqueous electrolytic solution contains the pentafluorophenyloxy compound in an amount of preferably not more than 10 wt. %, more preferably not more than 5 wt. %, and most preferably not more than 3 wt. %.

The compound represented by the formula (I) is contained in the non-aqueous electrolytic solution. Examples of the compound are described below.

In the formula (I), $R_1$ can be an alkylcarbonyl group having 2 to 12 carbon atoms. Examples of the alkylcarbonyl groups include methylcarbonyl, ethylcarbonyl, propylcarbonyl, butylcarbonyl, pentylcarbonyl, hexylcarbonyl, heptylcarbonyl, octylcarbonyl, nonylcarbonyl, decylcarbonyl and dodecylcarbonyl. The alkylcarbonyl groups further include branched alkylcarbonyl groups such as isopropylcarbonyl, tert-butylcarbonyl and 2-ethylhexylcarbonyl. At least one hydrogen atom of the substituent can be substituted with a halogen atom or an aryl group having 6 to 18 carbon atoms. Examples of the substituted alkylcarbonyl groups include trifluoromethylcarbonyl, 1,2-dichloroethylcarbonyl, pentafluoroethylcarbonyl, heptafluoropropylcarbonyl and benzylcarbonyl. The alkylcarbonyl group can have an unsaturated bond such as methylene ($CH_2$=) or allyl ($CH_2$=CH—$CH_2$—). Examples thereof include vinylcarbonyl and 1-methylvinylcarbonyl.

Preferred examples of the pentafluorophenyloxy compounds having an alkylcarbonyl group include pentafluorophenyl acetate, pentafluorophenyl propionate, pentafluorophenyl butyrate, pentafluorophenyl trifluoroacetate, pentafluorophenyl pentafluoropropionate, pentafluorophenyl acrylate and pentafluorophenyl methacrylate.

$R_1$ can be an alkoxycarbonyl group having 2 to 12 carbon atoms. Examples of the alkoxycarbonyl groups include methoxycarbonyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, decyloxycarbonyl and dodecyloxycarbonyl. The alkoxycarbonyl groups further include branched alkoxycarbonyl groups such as isopropoxycarbonyl, tert-butoxycarbonyl and 2-ethylhexyloxycarbonyl. At least one hydrogen atom of the substituent can be substituted with a halogen atom or an aryl group having 6 to 18 carbon atoms. Preferred examples of the substituted alkoxycarbonyl groups include 1-chloroethoxycarbonyl, 2-chloroethoxycarbonyl, 2,2,2-trifluoroethoxycarbonyl, 2,2,2-trichloroethoxycarbonyl and benzyloxycarbonyl.

Examples of the pentafluorophenyloxy compounds having an alkoxycarbonyl group include methyl pentafluorophenyl carbonate, ethyl pentafluorophenyl carbonate, tert-butyl pentafluorophenyl carbonate, 9-fluorenylmethyl pentafluorophenyl carbonate and 2,2,2-trifluoroethyl pentafluorophenyl carbonate.

$R_1$ can be an aryloxycarbonyl group having 7 to 18 carbon atoms. Examples of the aryloxycarbonyl groups include phenyloxycarbonyl, o-, m- or p-tolyloxycarbonyl.

Preferred examples of the pentafluorophenyloxy compounds having an aryloxycarbonyl group include phenyl pentafluorophenyl carbonate and dipentafluorophenyl carbonate.

$R_1$ can be an alkanesulfonyl group having 1 to 12 carbon atoms. Examples of the alkanesulfonyl groups include methanesulfonyl, ethanesulfonyl, propanesulfonyl, butanesulfonyl, pentanesulfonyl, hexanesulfonyl, heptanesulfonyl, octanesulfonyl, nonanesulfonyl, decanesulfonyl and dodecanesulfonyl. The alkanesulfonyl groups further include branched alkanesulfonyl groups such as 2-propanesulfonyl. At least one hydrogen atom of the substituent can be substituted with a halogen atom. Examples of the substituted alkanesulfonyl groups include trifluoromethanesulfonyl and 2,2,2-trifluoroethanesulfonyl.

Preferred examples of the pentafluorophenyloxy compounds having an alkanesulfonyl group include pentafluorophenyl methanesulfonate, pentafluorophenyl ethanesulfonate, pentafluorophenyl propanesulfonate, pentafluorophenyl trifluoromethanesulfonate and pentafluorophenyl 2,2,2-trifluoroethanesulfonate.

In the present invention, a non-aqueous electrolytic solution contains vinylene carbonate and/or 1,3-propanesultone in addition to the pentafluorophenyloxy compound. The non-aqueous electrolytic solution contains the vinylene carbonate and/or 1,3-propanesultone in an amount of preferably not less than 0.01 wt. %, more preferably not less than 0.1 wt. %, and most preferably not less than 0.5 wt. %. The non-aqueous electrolytic solution contains the vinylene carbonate and/or 1,3-propanesultone in an amount of preferably not more than 10 wt. %, more preferably not more than 5 wt. %, and most preferably not more than 3 wt. %.

A non-aqueous solvent is used in the non-aqueous electrolytic solution. Examples of the non-aqueous solvent include: cyclic carbonates such as ethylene carbonate (EC), propylene carbonate (PC), butylene carbonate (BC), dimethylvinylene carbonate (DMVC) and vinylethylene carbonate (VEC); lactones such as γ-butyrolactone (GBL), γ-valerolactone, and α-angelica lactone; linear carbonates such as dimethyl carbonate (DMC), methyl ethyl carbonate (MEC), diethyl carbonate (DEC), methyl propargyl carbonate (MPC), ethyl propargyl carbonate (EPC), and dipropargyl carbonate (DPC); ethers such as tetrahydrofuran, 2-methyltetrahydrofuran, 1,4-dioxane, 1,2-diethoxyethane, and 1,2-dibutoxyethane; nitriles such as acetonitrile; linear esters such as methyl propionate, methyl pivalate, butyl pivalate (PAB), hexyl pivalate, and octyl pivalate; amides such as dimethylformamide; and compounds having the S=O bonding such as propargyl methanesulfonate, glycol sulfite, dipropargyl sulfite, methyl propargyl sulfite, and divinyl sulfone.

The non-aqueous solvents can be mixed. Examples of combinations of the non-aqueous solvents include a combination of a cyclic carbonate and a linear carbonate, a combination of a cyclic carbonate and a lactone, a combination of a cyclic carbonate, a lactone and a linear ester, a combination of a cyclic carbonate, a linear carbonate and a lactone, a combination of a cyclic carbonate, a linear carbonate and an ether, and a combination of a cyclic carbonate, a linear carbonate and a linear ester. Preferred are the combination of the cyclic carbonate and the linear carbonate, and the combination of the cyclic carbonate, the lactone and the linear ester.

The non-aqueous solvent preferably contains at least one triple bond compound in addition to other solvent. Examples of the triple bond compounds include methyl propargyl carbonate (MPC), ethyl propargyl carbonate (EPC), dipropargyl carbonate (DPC), dipropargyl oxalate (DPO), propargyl methanesulfonate, dipropargyl sulfite and methyl propargyl sulfite. In the case that a density of an electrode composite increases in a battery of a high capacity, it can be observed that cycle characteristics are degraded. The triple bond compound is preferably used in addition to the pentafluorophenyloxy compound according to the present invention to improve the cycle characteristics.

The non-aqueous electrolytic solvent contains the triple bond compound in an amount of preferably not less than 0.01 wt. %, more preferably not less than 0.1 wt. %, and most preferably not less than 0.5 wt. %. The non-aqueous electrolytic solution contains the triple bond compound in an amount of preferably not more than 10 wt. %, more preferably not more than 5 wt. %, and most preferably not more than 3 wt. %.

An electrolyte salt is used in the present invention. Examples of the electrolyte salt include $LiPF_6$, $LiBF_4$ and $LiClO_4$. Examples further include lithium salts comprising a chain alkyl group such as $LiN(SO_2CF_3)_2$, $LiN(SO_2C_2F_5)_2$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, and lithium salts comprising a cyclic alkylene group such as $(CF_2)_2(SO_2)_2NLi$, $(CF_2)_3(SO_2)_2NLi$. One electrolyte salt can be used in the solution. Further, two or more electrolyte salts can be used in combination. The concentration of the electrolyte salts dissolved in the non-aqueous solvent is preferably not less than 0.3 M, more preferably not less than 0.5 M, and most preferably not less than 0.7 M. The concentration is preferably not more than 2.5 M, more preferably not more than 1.5 M, and most preferably not more than 0.9 M.

The electrolytic solution can be obtained according to the invention, for example by mixing the non-aqueous solvents, dissolving the electrolyte salt in the mixture, dissolving the pentafluorophenyloxy compound in the solution, and dissolving vinylene carbonate and/or 1,3-propanesultone in the solution.

The non-aqueous electric solution according to the invention can contain air or carbon dioxide to inhibit generation of a gas caused by decomposition of the electrolytic solution and to improve battery performance such as cycle and storage characteristics.

Carbon dioxide or air can be incorporated (dissolved) in the non-aqueous electrolytic solution in the present invention according to a method (1) of contacting the non-aqueous electrolytic solution to air or a carbon dioxide-containing gas to introduce the air or the gas into the solution, and then injecting the solution into the battery, or a method of (2) injecting the non-aqueous electrolytic solution into the battery, and then introducing air or a carbon dioxide-containing gas into the battery before or after sealing the battery. The two methods can be used in combination. The amount of the moisture contained in the air or carbon dioxide-containing gas is preferably as small as possible. The amount of the moisture is so reduced that the due point of the air or gas is lower than −40° C., and more preferably lower than −50° C.

The non-aqueous electrolytic solution according to the present invention can further contain at least one aromatic compound to prevent the battery from excessive charge. Examples of the aromatic compounds include cyclohexylbenzene, 1-fluoro-2-cyclohexylbenzene, 1-fluoro-3-cyclohexylbenzene, 1-fluoro-4-cyclohexylbenzene, biphenyl, o-terphenyl, tert-butylbenzene, 1,3-di-tert-butylbenzene, 1-fluoro-4-tert-butylbenzene, tert-pentylbenzene, a partially hydrogenated o-terphenyl (such as 1,2-dicyclohexylbenzene, 2-phenylbicyclohexyl, 1,2-diphenylcyclohexane, o-cyclohexylbiphenyl), a partially hydrogenated m-terphenyl (examples analogous to the examples of the partially hydrogenated o-terphenyl) and a partially hydrogenated p-terphenyl (examples analogous to the examples of the partially hydrogenated o-terphenyl). The non-aqueous electrolytic solution contains the aromatic compound preferably in an amount of 0.1 to 5 wt. %.

The non-aqueous electrolytic solution according to the present invention is used as a material of a secondary battery, particularly a lithium secondary battery. There is no specific limitation with respect to materials of the lithium secondary battery other than the non-aqueous electrolytic solution according to the present invention. The materials of the conventional lithium secondary battery can be used in the present invention.

An active positive electrode material preferably is complex oxide of lithium with cobalt or nickel. Only one material can be selected and used as the active positive electrode material. Further, two or more active positive electrode materials can be used in combination. Examples of the complex lithium oxide include $LiCoO_2$, $LiNiO_2$, $LiCo_{1-x}Ni_xO_2$ ($0.01<x<1$) and $LiMn_2O_4$. The two or more active positive electrode materials can be mixed in an appropriate way. Examples of the mixtures include a mixture of $LiCoO_2$ with $LiMn_2O_4$, a mixture of $LiCoO_2$ with $LiNiO_2$, and a mixture of $LiMn_2O_4$ with $LiNiO_2$.

The positive electrode can be formed by mixing the active positive electrode material with conductive materials such as acetylene black or carbon black, and a binder to prepare a positive electrode composite material, coating a collecting material with the positive electrode material, drying the electrode material, pressing and molding them, and heating them at a temperature of 50 to 250° C. for about 2 hours under reduced pressure. Examples of the binder include polytetrafluoroethylene (PTFE), polyvinylidene fluoride (PVDF), styrene/butadiene copolymer (SBR), acrylonitrile/butadiene copolymer (NBR), and carboxymethylcellulose (CMC). Examples of the collecting material include aluminum foil and a stainless lath board.

A material capable of absorbing and releasing lithium can be used as a negative electrode. Examples of the material include: a carbonaceous material such as thermally decomposed carbon, coke, graphite (e.g., artificial graphite, natural graphite) a combustion product of an organic polymeric compound, or carbon fiber; tin or a tin compound, and silicon or a silicon compound. The carbonaceous material preferably has a distance ($d_{002}$) between lattice faces (002) of 0.340 nm or less. The carbonaceous material more preferably is graphite having a graphitic crystal structure with the distance ($d_{002}$) in the range of 0.335 to 0.340 nm. One material can be selected and used as the active negative electrode material. Further, two or more active negative electrode materials can be used in combination. A powdery material such as that of carbonaceous material can be used as a negative electrode composite material by mixing the material with a binder. Examples of the binder include ethylene/propylene diene terpolymer (EPDM), polytetrafluoroethylene (PTFE), polyvinylidene fluoride (PVDF), styrene/butadiene copolymer (SBR), acrylonitrile/butadiene copolymer (NBR), and carboxymethyl-cellulose (CMC). There is no specific limitation with respect to the method for forming the negative electrode. The negative electrode can be prepared in the same manner as in the above-mentioned method for forming the positive electrode.

The effect obtained by addition of the compound according to the present invention is large in a lithium secondary battery comprising an electrode composite of high density. The positive electrode composite layer formed on aluminum foil has a density of preferably not smaller than 3.2 g/cm$^3$, more preferably not smaller than 3.3 g/cm$^3$, and most preferably not smaller than 3.4 g/cm$^3$. If the density of the positive electrode is more than 4.0 g/cm$^3$, it is difficult to prepare the battery. The positive electrode composite layer has a density of preferably not larger than 4.0 g/cm$^3$, more preferably not larger than 3.9 g/cm$^3$, and most preferably not larger than 3.8 g/cm$^3$. The negative electrode composite layer formed on copper foil has a density of preferably not smaller than 1.3 g/cm$^3$, more preferably not smaller than 1.4 g/cm$^3$, and most preferably not smaller than 1.5 g/cm$^3$. If the density of the negative electrode is more than 2.0 g/cm$^3$, it is difficult to prepare the battery. The negative electrode composite layer has a density of preferably not larger than 2.0 g/cm$^3$, more preferably not larger than 1.9 g/cm$^3$, and most preferably not larger than 1.8 g/cm$^3$.

If the thickness (per one side of the collector) of the positive electrode layer in the lithium secondary battery according to the present invention is small, the quantity of an active material in the electrode material layer is lowered to decrease the battery capacity. The positive electrode layer has a thickness of preferably not smaller than 30 μm, and more preferably not smaller than 50 μm. If the thickness of the positive electrode layer is large, the cycle characteristics or the rate characteristics are unfavorably degraded. The positive electrode layer has a thickness of preferably not larger than 120 μm, and more preferably not larger than 100 μm.

If the thickness (per one side of the collector) of the negative electrode layer is small, the quantity of an active material in the electrode material layer is lowered to decrease the battery capacity. The negative electrode layer has a thickness of preferably not smaller than 1 μm, and more preferably not smaller than 3 μm. If the thickness of the negative electrode layer is large, the cycle characteristics or the rate characteristics are unfavorably degraded. The positive electrode layer has a thickness of preferably not larger than 100 μm, and more preferably not larger than 70 μm.

There is no specific limitation with respect to the structure of the lithium secondary battery. Examples of the structure include a coin-shaped battery, a cylindrical battery, and a square-shaped battery. The coin-shaped battery comprises a positive electrode, a negative electrode, and a single-layered or a multi-layered separator. The cylindrical or square-shaped battery comprises a positive electrode, a negative electrode and a rolled separator. A known separator such as a minute porous material of polyolefin, a fabric, and a non-woven fabric can be used.

The lithium secondary battery according to the present invention shows excellent cycle characteristics for a long term even if the charging termination voltage is higher such as 4.2 V. The battery further shows excellent cycle characteristics even if the charging termination voltage is higher than 4.3 V. The discharging termination voltage can be 2.5 V or more, and further can be 2.8 V or more. There is no specific limitation with respect to the current level. The battery is generally discharged at a constant current of 0.1 to 3 C. The lithium secondary battery according to the present invention can be charged and discharged at a temperature in a wide range of −40° C. to 100° C. The battery is preferably charged and discharged at a temperature of 0° C. to 80° C.

A safety valve can be attached to a sealing plate to prevent the lithium secondary battery from increasing the inner pressure. A part of the battery such as a battery cell (can) or a gasket can be cut to prevent pressure increase. At least one of various conventional safety attachments (for example overcurrent-preventing devices such as a fuse, a bimetal and a PTC device) is preferably attached to the battery.

Two or more lithium secondary batteries according to the present invention can-be placed in a battery package while arranging the batteries in series and/or parallel. A safety circuit (which has functions of monitoring conditions such as voltage, temperature and current in each of the battery or in the combined batteries, and breaking the current) can be attached to the battery package in addition to a safety attachment such as a PTC element, a thermal fuse, a fuse, and a current breaker.

EXAMPLES

The present invention is described by referring to the following examples and comparison examples.

Example 1

(Preparation of Non-Aqueous Electrolytic Solution)

A non-aqueous solvent of EC:PC:MEC having a volume ratio of 30:5:65 was prepared. LiPF$_6$ (electrolyte salt) was dissolved in the solvent to prepare a 0.9 M non-aqueous electrolytic solution. 0.5 wt. % of pentafluorophenyl methanesulfonate and 5 wt. % of vinylene carbonate were added to the non-aqueous electrolytic solution. The percentage was expressed based on the non-aqueous electrolytic solution.

(Preparation of Lithium Secondary Battery and Measurement of Battery Performance)

90 wt. % of LiCoO$_2$ (active positive electrode material), 5 wt. % of acetylene black (conductive material), and 5 wt. % of polyvinylidene fluoride (binder) were mixed. 1-methyl-2-pyrrolidone (solvent) was added to the mixture. A surface of aluminum foil was coated with the resulting solution. The mixture was dried, molded under pressure, and heated to form a positive electrode.

95 wt. % of artificial graphite (active negative electrode material) having a graphitic crystalline structure with a distance ($d_{002}$) of 0.335 nm between lattice faces (002), and 5 wt. % of polyvinylidene fluoride (binder) were mixed. 1-methyl-2-pyrrolidone (solvent) was added to the mixture. A surface of copper foil was coated with the resulting solution. The mixture was dried, molded under pressure and heated to form a negative electrode.

A battery was prepared using a separator comprising a micro porous polypropylene film. The non-aqueous electrolytic solution was poured into the battery. Carbon dioxide having the dew point of −60° C. was introduced into the battery to prepare a cylindrical battery having the 18650 size (diameter: 18 mm, height: 65 mm). A pressure release vent and an inner current breaker (PTC element) were attached to the battery. The positive electrode composition layer has a density of 3.6 g/cm$^3$, and the negative electrode composition layer has a density of 1.7 g/cm$^3$. The positive electrode layer has a thickness of 60 μm (per one side of the collector), and the negative electrode layer has a thickness of 60 μm (per one side of the collector).

The battery was charged with the constant current of 2.2 A (1C) at an ordinary temperature (20° C.) to reach 4.2 V. The battery was further charged under the constant voltage for 3 hours in total to reach the terminal voltage of 4.2 V. The battery was discharged under the constant current of 2.2 A (1C) to reach the terminal voltage of 2.8 V. The cycle of charge and discharge was repeated. The initial discharging capacity was the essentially same as that of Comparison Example 1 (using 0.9 M $LiPF_6$-EC:PC:MEC (volume ratio) =30:5:65 as the non-aqueous electrolytic solution in which pentafluorophenyl methane-sulfonate was not added). The battery performance was measured after 200 cycles. The retention of the discharging capacity relative to the initial discharging capacity (100%) was 84.9%. The conditions for preparation of the 18650 battery and the battery performance thereof are set forth in Table 1.

Example 2

An electrolytic solution and an 18650 battery were prepared in the same manner as in Example 1, except that 1 wt. % of pentafluorophenyl methanesulfonate and 2 wt. % of vinylene carbonate were added to the non-aqueous electrolytic solution. The battery performance was measured after 200 cycles. The retention of the discharging capacity relative to the initial discharging capacity was 85.1%. The conditions for preparation of the battery and the battery performance thereof are set forth in Table 1.

Example 3

An electrolytic solution and an 18650 battery were prepared in the same manner as in Example 1, except that 1 wt. % of pentafluorophenyl methanesulfonate, 2 wt. % of vinylene carbonate and 0.5 wt. % of dipropargyl oxalate were added to the non-aqueous electrolytic solution. The battery performance was measured after 200 cycles. The retention of the discharging capacity relative to the initial discharging capacity was 86.6%. The conditions for preparation of the battery and the battery performance thereof are set forth in Table 1.

Example 4

An electrolytic solution and an 18650 battery were prepared in the same manner as in Example 1, except that 5 wt. % of pentafluorophenyl methanesulfonate and 1 wt. % of vinylene carbonate were added to the non-aqueous electrolytic solution. The battery performance was measured after 200 cycles. The retention of the discharging capacity relative to the initial discharging capacity was 85.5%. The conditions for preparation of the battery and the battery performance thereof are set forth in Table 1.

Example 5

An electrolytic solution and an 18650 battery were prepared in the same manner as in Example 1, except that 1 wt. % of pentafluorophenyl acetate and 2 wt. % of vinylene carbonate were added to the non-aqueous electrolytic solution. The battery performance was measured after 200 cycles. The retention of the discharging capacity relative to the initial discharging capacity was 84.9%. The conditions for preparation of the battery and the battery performance thereof are set forth in Table 1.

Example 6

An electrolytic solution and an 18650 battery were prepared in the same manner as in Example 1, except that 1 wt. % of methyl pentafluorophenyl carbonate and 2 wt. % of vinylene carbonate were added to the non-aqueous electrolytic solution. The battery performance was measured after 200 cycles. The retention of the discharging capacity relative to the initial discharging capacity was 84.5%. The conditions for preparation of the battery and the battery performance thereof are set forth in Table 1.

Example 7

An electrolytic solution and an 18650 battery were prepared in the same manner as in Example 1, except that 1 wt. % of pentafluorophenyl methanesulfonate, 1 wt. % of vinylene carbonate and 1 wt. % of 1,3-propanesultone (PS) were added to the non-aqueous electrolytic solution. The battery performance was measured after 200 cycles. The retention of the discharging capacity relative to the initial discharging capacity was 87.0%. The conditions for preparation of the battery and the battery performance thereof are set forth in Table 1.

Example 8

An electrolytic solution and an 18650 battery were prepared in the same manner as in Example 1, except that 1 wt. % of pentafluorophenyl methanesulfonate, 1 wt. % of vinylene carbonate, 1 wt. % of 1,3-propanesultone, 1 wt. % of cyclohexylbenzene and 1 wt. % of 1-fluoro-4-cyclohexylbenzene were added to the non-aqueous electrolytic solution. The battery performance was measured after 200 cycles. The retention of the discharging capacity relative to the initial discharging capacity was 86.8%. The conditions for preparation of the battery and the battery performance thereof are set forth in Table 1.

Example 9

An electrolytic solution and an 18650 battery were prepared in the same manner as in Example 1, except that 1 wt. % of pentafluorophenyl methanesulfonate, 1 wt. % of vinylene carbonate, 1 wt. % of 1,3-propanesultone, 1 wt. % of cyclohexylbenzene and 1 wt. % of tert-pentylbenzene were added to the non-aqueous electrolytic solution. The battery performance was measured after 200 cycles. The retention of the discharging capacity relative to the initial discharging capacity was 86.7%. The conditions for preparation of the battery and the battery performance thereof are set forth in Table 1.

Example 10

An electrolytic solution and an 18650 battery were prepared in the same manner as in Example 1, except that $LiMn_2O_4$ was used as an active positive electrode material in place of $LiCoO_2$, EC/DEC (volume ratio: 30/70) was used as an non-aqueous solvent, and 1 wt. % of pentafluorophenyl methanesulfonate and 2 wt. % of 1,3-propanesultone were added to the non-aqueous electrolytic solution. The battery performance was measured after 200 cycles. The retention of the discharging capacity relative to the initial discharging capacity was 81.2%. The conditions for preparation of the battery and the battery performance thereof are set forth in Table 1.

Reference Example 1

A non-aqueous solvent of EC:PC:MEC having a volume ratio of 30:5:65 was prepared. $LiPF_6$ (electrolyte salt) was dissolved in the solvent to prepare a 0.9 M non-aqueous electrolytic solution. 2 wt. % of pentafluorophenyl methanesulfonate was added to the non-aqueous electrolytic solution. Neither vinylene carbonate nor 1,3-propanesultone was added.

An 18650 battery were prepared in the same manner as in Example 1, except that the prepared non-aqueous electrolytic solution was used. The battery performance was measured after 200 cycles. The retention of the discharging capacity relative to the initial discharging capacity was 67.3%. The conditions for preparation of the battery and the battery performance thereof are set forth in Table 1.

Comparison Example 1

A non-aqueous solvent of EC:PC:MEC having a volume ratio of 30:5:65 was prepared. $LiPF_6$ (electrolyte salt) was dissolved in the solvent to prepare a 0.9 M non-aqueous electrolytic solution. 2 wt. % of vinylene carbonate was added to the non-aqueous electrolytic solution.

An 18650 battery were prepared in the same manner as in Example 1, except that the prepared non-aqueous electrolytic solution was used. The battery performance was measured after 200 cycles. The retention of the discharging capacity relative to the initial discharging capacity was 68.9%. The conditions for preparation of the battery and the battery performance thereof are set forth in Table 1.

Comparison Example 2

A non-aqueous solvent of EC:PC:MEC having a volume ratio of 30:5:65 was prepared. $LiPF_6$ (electrolyte salt) was dissolved in the solvent to prepare a 0.9 M non-aqueous electrolytic solution. 2 wt. % of 1,3-propanesultone was added to the non-aqueous electrolytic solution.

An 18650 battery were prepared in the same manner as in Example 1, except that the prepared non-aqueous electrolytic solution was used. The battery performance was measured after 200 cycles. The retention of the discharging capacity relative to the initial discharging capacity was 66.9%. The conditions for preparation of the battery and the battery performance thereof are set forth in Table 1.

Comparison Example 3

A non-aqueous solvent of EC:PC:MEC having a volume ratio of 30:5:65 was prepared. $LiPF_6$ (electrolyte salt) was dissolved in the solvent to prepare a 0.9 M non-aqueous electrolytic solution. 1 wt. % of pentafluoroanisole and 2 wt. %, of vinylene carbonate were added to the non-aqueous electrolytic solution.

An 18650 battery were prepared in the same manner as in Example 1, except that the prepared non-aqueous electrolytic solution was used. The battery performance was measured after 200 cycles. The retention of the discharging capacity relative to the initial discharging capacity was 70.1%. The conditions for preparation of the battery and the battery performance thereof are set forth in Table 1.

TABLE 1

| | | Positive electrode | Compound A (amount: wt. %) |
|---|---|---|---|
| Example | | | |
| | 1 | $LiCoO_2$ | Pentafluorophenyl methanesulfonate (0.5) |
| | 2 | $LiCoO_2$ | Pentafluorophenyl methanesulfonate (1) |
| | 3 | $LiCoO_2$ | Pentafluorophenyl methanesulfonate (1) Dipropargyl oxalate (0.5) |
| | 4 | $LiCoO_2$ | Pentafluorophenyl methanesulfonate (5) |
| | 5 | $LiCoO_2$ | Pentafluorophenyl acetate (1) |
| | 6 | $LiCoO_2$ | Methyl pentafluorophenyl carbonate (1) |
| | 7 | $LiCoO_2$ | Pentafluorophenyl methanesulfonate (1) |
| | 8 | $LiCoO_2$ | Pentafluorophenyl methanesulfonate (1) |
| | 9 | $LiCoO_2$ | Pentafluorophenyl methanesulfonate (1) |
| | 10 Reference example | $LiMn_2O_4$ | Pentafluorophenyl methanesulfonate (1) |
| | 1 Comparison example | $LiCoO_2$ | Pentafluorophenyl methanesulfonate (2) |
| | 1 | $LiCoO_2$ | None |
| | 2 | $LiCoO_2$ | None |
| | 3 | $LiCoO_2$ | Pentafluoroanisole (1) |

| | | Amount of VC | Amount of PS | Composition of electrolytic solution (volume ratio) |
|---|---|---|---|---|
| Example | | | | |
| | 1 | 5 wt. % | 0 wt. % | 0.9M $LiPF_6$ (EC/PC/MEC = 30/5/65) |
| | 2 | 2 wt. % | 0 wt. % | 0.9M $LiPF_6$ (EC/PC/MEC = 30/5/65) |
| | 3 | 2 wt. % | 0 wt. % | 0.9M $LiPF_6$ (EC/PC/MEC = 30/5/65) |
| | 4 | 1 wt. % | 0 wt. % | 0.9M $LiPF_6$ (EC/PC/MEC = 30/5/65) |
| | 5 | 2 wt. % | 0 wt. % | 0.9M $LiPF_6$ (EC/PC/MEC = 30/5/65) |
| | 6 | 2 wt. % | 0 wt. % | 0.9M $LiPF_6$ (EC/PC/MEC = 30/5/65) |
| | 7 | 1 wt. % | 1 wt. % | 0.9M $LiPF_6$ (EC/PC/MEC = 30/5/65) |
| | 8 | 1 wt. % | 1 wt. % | 0.9M $LiPF_6$ (EC/PC/MEC = 30/5/65) |
| | 9 | 1 wt. % | 1 wt. % | 0.9M $LiPF_6$ (EC/PC/MEC = 30/5/65) |
| | 10 Reference example | 0 wt. % | 2 wt. % | 0.9M $LiPF_6$ (EC/DEC = 30/70) |
| | 1 Comparsion example | 0 wt. % | 0 wt. % | 0.9M $LiPF_6$ (EC/PC/MEC = 30/5/65) |
| | 1 | 2 wt. % | 0 wt. % | 0.9M $LiPF_6$ (EC/PC/MEC = 30/5/65) |
| | 2 | 0 wt. % | 2 wt. % | 0.9M $LiPF_6$ (EC/PC/MEC = 30/5/65) |
| | 3 | 2 wt. % | 0 wt. % | 0.9M $LiPF_6$ (EC/PC/MEC = 30/5/65) |

| | | Compound B (amount: wt. %) | Initial discharging capacity | Retention of discharging capacity |
|---|---|---|---|---|
| Example | | | | |
| | 1 | None | 1.00 | 84.9 |
| | 2 | None | 1.01 | 85.1 |
| | 3 | None | 1.01 | 86.6 |
| | 4 | None | 1.01 | 85.5 |
| | 5 | None | 1.00 | 84.9 |
| | 6 | None | 1.00 | 84.5 |
| | 7 | None | 1.01 | 87.0 |
| | 8 | Cyclohexylbenzene (1) 1-F-4-cyclohexylbenzene (1) | 1.01 | 86.8 |
| | 9 | Cyclohexylbenzene (1) Tert-pentylbenzene (1) | 1.01 | 86.7 |
| | 10 Reference example | None | 0.87 | 81.2 |
| | 1 Comparison example | None | 1.00 | 67.3 |
| | 1 | None | 1 | 68.9 |
| | 2 | None | 1.00 | 66.9 |
| | 3 | None | 1.00 | 70.1 |

(Remark)
1-F-4-cyclohexylbenzene: 1-fluoro-4-cyclohexylbenzene
Initial discharging capacity: relative value
Retention of discharging capacity: after 200 cycles

Example 11

A non-aqueous solvent of EC:GBL:butyl pivalate (PAB) having a volume ratio of 20:75:5 was prepared. 0.9 M of $LiPF_6$ and 0.1 M of $LiBF_4$ were dissolved in the solvent to prepare a non-aqueous electrolytic solution. 1 wt. % of pentafluorophenyl methanesulfonate and 3 wt. % of vinylene carbonate were added to the non-aqueous electrolytic solution.

An 18650 battery were prepared in the same manner as in Example 1, except that the prepared non-aqueous electrolytic solution was used. The battery performance was measured after 100 cycles. The retention of the discharging capacity relative to the initial discharging capacity was 80.2%. The conditions for preparation of the battery and the battery performance thereof are set forth in Table 2.

Example 12

A non-aqueous solvent of EC:GBL:PAB having a volume ratio of 20:75:5 was prepared. 0.9 M of $LiPF_6$ and 0.1 M of $LiBF_4$ were dissolved in the solvent to prepare a non-aqueous electrolytic solution. 1 wt. % of pentafluorophenyl methanesulfonate, 3 wt. % of vinylene carbonate and 0.5 wt. % of 1,3-propanesultone were added to the non-aqueous electrolytic solution.

An 18650 battery were prepared in the same manner as in Example 1, except that the prepared non-aqueous electrolytic solution was used. The battery performance was measured after 100 cycles. The retention of the discharging capacity relative to the initial discharging capacity was 81.3%. The conditions for preparation of the battery and the battery performance thereof are set forth in Table 2.

Comparison Example 4

A non-aqueous solvent of EC:GBL:PAB having a volume ratio of 20:75:5 was prepared. 0.9 M of $LiPF_6$ and 0.1 M of $LiBF_4$ were dissolved in the solvent to prepare a non-aqueous electrolytic solution. 3 wt. % of vinylene carbonate was added to the non-aqueous electrolytic solution.

An 18650 battery were prepared in the same manner as in Example 1, except that the prepared non-aqueous electrolytic solution was used. The battery performance was measured after 100 cycles. The retention of the discharging capacity relative to the initial discharging capacity was 30.7%. The conditions for preparation of the battery and the battery performance thereof are set forth in Table 2.

The present invention is not limited to the examples described above. The various combinations can be possible according to the invention. Particularly, the combinations of solvents cannot be limited to the examples. Further, the present invention can be applied to a cylindrical or square-shaped battery, though the Examples relate to the 18650 battery.

The invention claimed is:

1. A non-aqueous electrolytic solution comprising an electrolyte salt in a non-aqueous solvent, wherein the non-aqueous electrolytic solution further contains a pentafluorophenyloxy compound represented by the formula (I), and vinylene carbonate and/or 1,3-propanesultone:

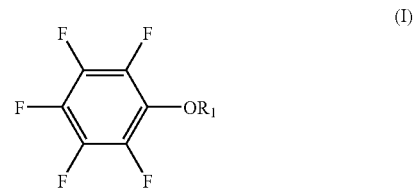

(I)

in which $R_1$ is a substituent selected from the group consisting of an alkylcarbonyl group having 2 to 12 carbon atoms, an alkoxycarbonyl group having 2 to 12 carbon atoms, an aryloxycarbonyl group having 7 to 18 carbon atoms, and an alkanesulfonyl group having 1 to 12 carbon atoms, and at least one hydrogen atom of the substituent can be substituted with a halogen atom or an aryl group having 6 to 18 carbon atoms.

2. The non-aqueous electrolytic solution of claim 1, wherein $R_1$ in the formula (I) is an alkanesulfonyl group having 1 to 12 carbon atoms.

3. The non-aqueous electrolytic solution of claim 1, wherein $R_1$ in the formula (I) is an alkanesulfonyl group having 1 to 6 carbon atoms.

4. The non-aqueous electrolytic solution of claim 1, wherein $R_1$ in the formula (I) is methanesulfonyl.

5. The non-aqueous electrolytic solution of claim 1, wherein the solution contains the pentafluorophenyloxy compound represented by the formula (I) in an amount of 0.01 to 10 wt. %.

TABLE 2

| | Positive electrode | Amount of Compound* | Amount of VC | Amount of PS | Initial discharging capacity | Retention of discharging capacity |
|---|---|---|---|---|---|---|
| Example | | | | | | |
| 11 | $LiCoO_2$ | 1 wt. % | 3 wt. % | 0 wt. % | 1.00 | 80.2 |
| 12 | $LiCoO_2$ | 1 wt. % | 3 wt. % | 0.5 wt. % | 1.00 | 81.3 |
| Comparison example | | | | | | |
| 4 | $LiCoO_2$ | 0 wt. % | 3 wt. % | 0 wt. % | 1.00 | 30.7 |

(Remark)
Composition of electrolytic solution (volume ratio) used in Examples 11, 12 and Comparison example 4: 1M $LiPF_6$/$LiBF_4$ = 9/1 (EC/GBL/PAB = 20/75/5)
Compound*: Pentafluorophenyl methanesulfonate Initial discharging capacity: relative value
Retention of discharging capacity: after 100 cycles 6. The non-aqueous electrolytic solution of claim 1, wherein the solution contains the pentafluorophenyloxy compound represented by the formula (I) in an amount of 0.1 to 5 wt. %.

7. The non-aqueous electrolytic solution of claim 1, wherein the solution contains the vinylene carbonate and/or 1,3-propanesultone in an amount of 0.01 to 10 wt. %.

8. The non-aqueous electrolytic solution of claim 1, wherein the solution contains the vinylene carbonate and/or 1,3-propanesultone in an amount of 0.1 to 5 wt. %.

9. The non-aqueous electrolytic solution of claim 1, wherein the solution further contains at least one compound selected from the group consisting of cyclohexylbenzene, 1-fluoro-2-cyclohexylbenzene, 1-fluoro-3-cyclohexylbenzene, 1-fluoro-4-cyclohexylbenzene, biphenyl, o-terphenyl, tert-butylbenzene, 1-fluoro-4-tert-butylbenzene, tert-pentylbenzene, a partially hydrogenated o-terphenyl, a partially hydrogenated m-terphenyl and a partially hydrogenated p-terphenyl.

10. A lithium secondary battery comprising a positive electrode, a negative electrode and a non-aqueous electrolytic solution comprising an electrolyte salt in a non-aqueous solvent, wherein the non-aqueous electrolytic solution further contains a pentafluorophenyloxy compound represented by the formula (I), and vinylene carbonate and/or 1,3-propanesultone:

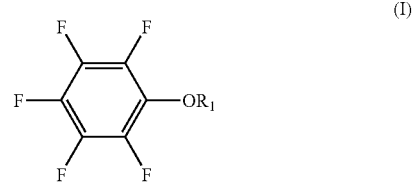

(I)

in which $R_1$ is a substituent selected from the group consisting of an alkylcarbonyl group having 2 to 12 carbon atoms, an alkoxycarbonyl group having 2 to 12 carbon atoms, an aryloxycarbonyl group having 7 to 18 carbon atoms, and an alkanesulfonyl group having 1 to 12 carbon atoms, and at least one hydrogen atom of the substituent can be substituted with a halogen atom or an aryl group having 6 to 18 carbon atoms.

* * * * *